(12) United States Patent
Sgaravatti et al.

(10) Patent No.: US 12,257,339 B2
(45) Date of Patent: Mar. 25, 2025

(54) **PHYTOCOMPLEX AND EXTRACT OF A MERISTEMATIC CELL LINE SELECTED FROM A PLANT BELONGING TO THE GENUS *ROSA***

(71) Applicant: AETHERA BIOTECH S.R.L., Camisano Vicentino (IT)

(72) Inventors: Elena Sgaravatti, Padua (IT); Giovanna Pressi, Rubano (IT); Flavia Guzzo, Verona (IT)

(73) Assignee: AETHERA BIOTECH S.R.L., Camisano Vicentino (IT)

( * ) Notice: Subject to any disclaimer, the term of this patent is extended or adjusted under 35 U.S.C. 154(b) by 801 days.

(21) Appl. No.: 17/441,224

(22) PCT Filed: Mar. 20, 2020

(86) PCT No.: PCT/IB2020/052584
§ 371 (c)(1),
(2) Date: Sep. 20, 2021

(87) PCT Pub. No.: WO2020/188531
PCT Pub. Date: Sep. 24, 2020

(65) Prior Publication Data
US 2022/0175654 A1    Jun. 9, 2022

(30) Foreign Application Priority Data
Mar. 21, 2019 (IT) .................. 102019000004105

(51) Int. Cl.
*A61K 36/738* (2006.01)
*A61K 8/9783* (2017.01)
*A61K 9/00* (2006.01)
*A61Q 19/08* (2006.01)

(52) U.S. Cl.
CPC .......... *A61K 8/9783* (2017.08); *A61K 9/0014* (2013.01); *A61K 36/738* (2013.01); *A61Q 19/08* (2013.01)

(58) Field of Classification Search
CPC .................................................. A61K 36/738
See application file for complete search history.

(56) References Cited

U.S. PATENT DOCUMENTS

2009/0208544 A1   8/2009  Ennamany et al.
2014/0356310 A1*  12/2014  Paris ................. A61K 8/9783
                                                                        435/410

FOREIGN PATENT DOCUMENTS

CN     107496346 A  * 12/2017  ............... A61K 8/60
WO     2013102882 A2    7/2013

OTHER PUBLICATIONS

Khosh-Khui et al.: "In Vitro Culture of the *Rosa* Species", Floriculture, Ornamental and Plant Biotechnology, vol. II, pp. 512-526, Dec. 1, 2006.
Visessuwan et al.: "Plant regeneration systems from leaf segment culture through embryonic callus formation of Rosa hybrida and R. cania", Breeding Science, vol. 47, No. 3, 1997, pp. 217-222.
Lattanzio et al.: "In vivo anti-inflammatory effect of Rosa canina L. extract", Journal of Ethnopharmacology, Elsevier Ireland Ltd, IE, Feb. 1, 2021, pp. 880-885.
Cornelia et al.: "Potential of plant cells in culture for cosmetic application", Phytochemistry Reviews, vol. 7, No. 3, Dec. 1, 2007, pp. 559-605.
Rout et al.: "Biotechnology of the rose: A review of recent progress", Scientia Horticulturae, Elsevier, Amsterdam, NL, vol. 81, No. 3, Sep. 1, 1999, pp. 201-228.
International Search Report and Written Opinion for PCT/IB2020/052584, mailed May 29, 2020.

* cited by examiner

*Primary Examiner* — Qiuwen Mi
(74) *Attorney, Agent, or Firm* — Procopio, Cory, Hargreaves & Savitch LLP; Brent A. Johnson; Erica A. Spence

(57) ABSTRACT

The present invention relates to a meristematic cell line selected from tissue, preferably callus tissue, of a plant belonging to the genus *Rosa*. The invention also relates to a derivative of the cell line, i.e. a phytocomplex or an extract of the cell line. The meristematic cell line is characterized by a high polysaccharide content. Furthermore, the present invention relates to the cosmetic, nutraceutical and medical use of the selected meristematic cell line or of a derivative thereof.

20 Claims, 9 Drawing Sheets

| id | m/z (-) | m/z (+) | putative identification |
|---|---|---|---|
| 1 | | 331 355 | galloyl hexose |
| 2 | | 487 | gallic acid derivative |
| 3 | | 577 | procyanidin P2 |
| 4 | | 865 | procyanidin P3 |
| 5 | | 289 291 | catechin/epicatechin |
| 6 | | 633 - | gallic acid derivative |
| 7 | | 325 349 | coumaric acid hexose |
| 8 | | 447 | ellagic acid deoxyhexose |
| 9 | | 463 | ellagic acid hexose |
| 10 | | 577 | procyanidin P2 |
| 11 | | 729 | procyanidin P2Pg |
| 12 | 935, 467 | | galloyl-bis-HHDP-glucose |
| 13 | | 433 | ellagic acid pentose |
| 14 | | 433 | ellagic acid pentose |
| 15 | | 493 | caffeic acid derivative |
| 16 | 934, 475, 1869 | | dimer of galloyl-bis-HHDP (M-2H)-- |
| 17 | 935, 467 | | galloyl-bis-HHDP-glucose |
| 18 | 449 935 | | tetrahydroxyflavanone-O-hexoxide, galloyl-bis- |
| 19 | 469, 939 | | ellagitannin (M-2H)-- |
| 20 | 477, 955 | | gallic acid derivative (M-2H)-- |
| 21 | | 507 | gallic acid derivative |
| 22 | | 586 | ellagic acid derivative |
| 23 | | 471 | coumaric acid derivative |
| 24 | | 711 | unidentified |
| 25 | | 471 | coumaric acid derivative |
| 26 | | 711 | unidentified |
| 27 | | 595 | tetrahydroxyflavanone-O-rutinoside |
| 28 | | 711 | unidentified |
| 29 | | 695 | unidentified |
| 30 | | 696 | unidentified |
| 31 | | 693 | unidentified |
| 32 | | 695 | unidentified |
| 33 | | 693 | unidentified |

Fig.8

PHYTOCOMPLEX AND EXTRACT OF A MERISTEMATIC CELL LINE SELECTED FROM A PLANT BELONGING TO THE GENUS *ROSA*

CROSS-REFERENCE TO RELATED APPLICATIONS

This application is a national phase application of PCT/IB2020/052584, filed on Mar. 20, 2020, which claims the benefit of Italian Patent Application No. 102019000004105, filed on Mar. 21, 2019 both of which are incorporated by reference herein in their entirety.

FIELD OF THE INVENTION

The present invention relates to a meristematic cell line, derived from a plant belonging to the genus *Rosa* characterized by a high polysaccharide content and the cosmetic, nutraceutical and medical use of said meristematic cell line or a derivative thereof.

PRIOR ART

Medium molecular weight polysaccharides, such as dextran, exert hydrating and anti-inflammatory activities and retain water with an osmotic mechanism, thus contributing to improving the mechanical properties of the skin and tissues. Furthermore, dextran, in association with other active ingredients and an appropriate vehicle, is capable of attenuating oedema and redness, also in individuals with sensitive skin, and of reducing skin aging and irritation due to the action of weak carboxylic acids. In the pharmaceutical field, dextran sulphate possesses antithrombotic and anticoagulant activities, and can also be used with topical applications to regulate cutaneous blood flow.

There are numerous plant sources containing medium molecular weight polysaccharides and the use of many of them is already known. The best known among them is Aloe vera, whose leaves, rich in polysaccharides, are widely used in the formulation of cosmetic preparations for increasing skin hydration.

The polysaccharides present in *Camellia sinensis* have also demonstrated to be active in skin hydration by increasing the expression of aquaporins.

Aquaporins are a family of membrane proteins which allow the passage of water and small solutes through cell membranes. In particular, aquaporin-3 plays a key role in modulating skin hydration, skin elasticity and the barrier function of the epidermis.

The preparation of standardized plant derivatives (i.e. extracts with a reproducible content of metabolites) poses numerous problems tied to the variability of the content of metabolites in different plant tissues, seasonal variability in the content and type of metabolites, contaminations by plant parasites, differences tied to the geographical growing areas and loss of the biological activity of the molecule during harvest, storage and extraction. The extreme variability in the content of phytoconstituents of plant preparations obtained directly from a plant, or parts thereof, by extraction negatively impacts the effectiveness of the same.

An alternative method for obtaining contaminant-free standardized plant phytocomplexes in industrial quantities is to use in vitro cell cultures. This technology makes it possible to solve the problems tied to the variability of plant extracts, since it provides preparations with a content of active substances that can be reproduced in a standardized manner. The present invention falls in the context of this technological platform and provides a selected meristematic cell line from which a phytocomplex (and also an extract) with a standardized, reproducible content of active substances can be derived.

The present invention provides a selected meristematic cell line and derivatives thereof from plants belonging to the genus *Rosa* with a high polysaccharide content.

SUMMARY OF THE INVENTION

A first aspect of the present invention relates to a meristematic cell line derived from a plant belonging to the genus *Rosa*, preferably to the species *Rosa canina* or to the species *Rosa chinensis*, the cell line being preferably derived from a callus tissue obtained from the plant itself.

A second aspect of the present invention relates to a derivative of the meristematic cell line, i.e. a phytocomplex or an extract of the cell line.

The meristematic cell line and a derivative thereof are characterized by a high content of polysaccharides, preferably with a medium molecular weight.

A third aspect of the invention relates to a composition comprising the meristematic cell line or a derivative thereof, in a mixture with excipients that are accepted from a cosmetic and/or pharmaceutical viewpoint.

The Applicant has demonstrated that the cell line or a derivative thereof has an antioxidant activity and is capable of increasing the biosynthesis of aquaporins, in particular aquaporin 3, both for topical applications on skin models and for systemic applications. Aquaporins are substances involved in maintaining skin hydration and in wound healing.

Therefore, the invention also relates to a cosmetic use of the meristematic cell line or a derivative thereof to protect the skin against the signs of aging and maintain skin hydration (hydrating activity). The line or a derivative thereof also have an anti-wrinkle and an antioxidant activity.

Furthermore, the meristematic cell line or a derivative thereof can be used in the treatment or prevention of pathological conditions affecting the skin, such as: reddening, irritations, topical inflammation or cracks, or to accelerate wound healing processes (i.e. to accelerate wound healing).

Another aspect of the present invention relates to a process for the preparation and selection of plant meristematic cells of *Rosa* with a high polysaccharide content.

BRIEF DESCRIPTION OF THE FIGURES

The present invention is described in detail below and illustrated by way of example with reference to the appended figures, in which:

FIG. 8 shows, for each component of the Rc-F2P phytocomplex, the assigned code (id), the value of m/z and the identification of the main peaks obtained by means of the diode array detector and the UPLC-MS chromatograms (qTOF) obtained in the positive and negative ionization modes.

DEFINITIONS

Figure 1:
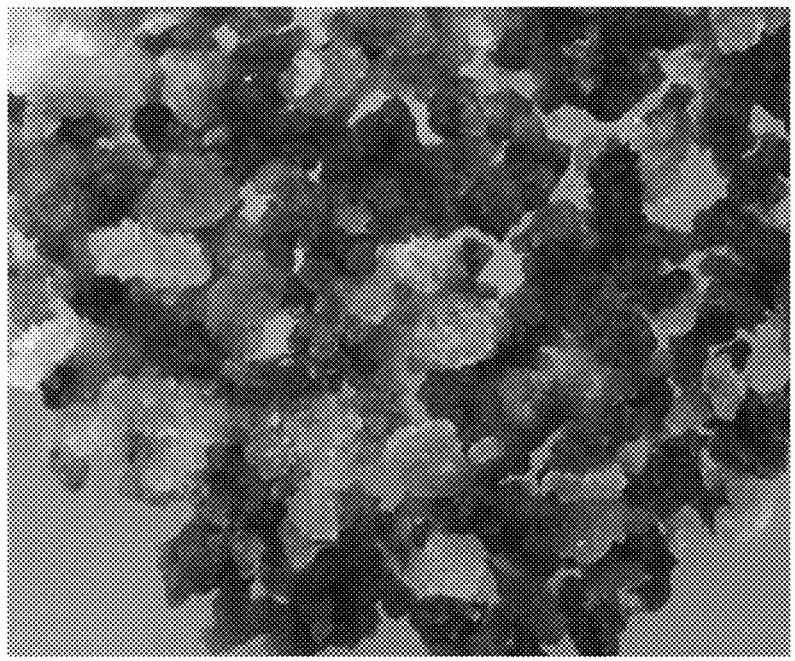
FIG. 1 shows a photo, taken with a bright-field optical microscope, of the cell line called Rc-F2P, maintained in a solid medium.

In the context of the present invention "meristematic line" or "meristematic cell" means a plant line or cell capable of maintaining the ability to divide by mitosis so as to originate new cells. Every meristematic cell derives from another meristematic cell. The function of plant meristematic cells is comparable to that of the stem cells in animals.

In the context of the present invention, "callus tissue" means a disorganized mass of undifferentiated or very scarcely specialized cells with thin cell walls and a large vacuole where secondary metabolites are accumulated.

In the context of the present invention, "medium molecular weight polysaccharides" means polysaccharides with a molecular weight comprised from 1000 to 5000 Da.

In the context of the present invention, "low molecular weight polysaccharides" means polysaccharides with a molecular weight of less than 1000 Da.

In the context of the present invention, unless specified otherwise, "w/w" means a weight/weight amount relative to the dry mass of the cell line.

DETAILED DESCRIPTION OF THE INVENTION

A first aspect of the present invention relates to a meristematic cell line derived from a plant belonging to the genus *Rosa*, preferably to the species *Rosa canina* or to the species *Rosa chinensis*.

In one embodiment, said meristematic cell line is obtained by means of a process that comprises the steps of:
1) plating a tissue obtained from a plant of the genus *Rosa* onto a solid culture medium;
2) isolating a plurality of cellular clones;
3) inoculating each of the isolated clones into a liquid culture medium;
4) determining the polysaccharide content for each clone;
5) selecting the cellular clone with the highest polysaccharide content.

In step 1), the tissue obtained from a plant of the genus *Rosa* is placed in a solid medium in order to obtain an undifferentiated callus tissue. The tissue of *Rosa* is preferably at least one shoot of *Rosa*, or a plurality of shoots of *Rosa*.

In a preferred embodiment of the invention, the solid and liquid culture media comprise salts suitable for the growth of plant cells, sucrose, naphthylacetic acid (NAA) and 6-benzyl amino purine (BAP).

The solid culture media further comprises agar, whereas the liquid culture media does not contain agar.

The solid and liquid culture media preferably each comprise sucrose in a concentration comprised from 10 to 45 g/L, preferably from 15 to 40 g/L; NAA in a concentration comprised from 0.5 to 2.5 mg/L, preferably from 0.8 to 2 mg/L, and BAP in a concentration comprised from 0.1 to 0.5 mg/L, preferably from 0.15 to 0.3 g/L.

In both the solid and liquid culture media, the salts suitable for the growth of plant cells are selected from: $CaCl_2$, $KNO_3$, $MgSO_4$, $NaH_2PO_4$, $(NH_4)_2SO_4$ and combinations thereof.

In both the solid and liquid culture media, the salts suitable for the growth of plant cells are preferably selected from: $CoCl_2 \cdot 6H_2O$, $CuSO_4 \cdot 5H_2O$, $NaEDTA \cdot 2H_2O$, $FeSO_4 \cdot 7H_2O$, $H_3BO_3$, KI, $MnSO_4 \cdot H_2O$, $Na_2MoO_4 \cdot 2H_2O$, $ZnSO_4 \cdot 7H_2O$ and combinations thereof.

Both the solid and liquid culture media further comprise vitamins suitable for the growth of plant cells, preferably selected from: myo-inositol, nicotinic acid, pyridoxine-HCl, thiamine-HCl and combinations thereof.

In one embodiment, in both the solid and liquid culture media, the salts suitable for the growth of plant cells are selected from: $CaCl_2$, $KNO_3$, $MgSO_4$, $NaH_2PO_4$, $(NH_4)_2SO_4$, $CoCl_2 \cdot 6H_2O$, $CuSO_4 \cdot 5H_2O$, $NaEDTA \cdot 2H_2O$, $FeSO_4 \cdot 7H_2O$ $H_3BO_3$, KI, $MnSO_4 \cdot H_2O$, $Na_2MoO_4 \cdot 2H_2O$, $ZnSO_4 \cdot 7H_2O$ and combinations thereof. This combination of salts is the medium Gamborg B5.

In one embodiment, both the solid and liquid culture media, in addition to the salts specified above, further comprise vitamins suitable for the growth of plant cells selected from: myo-inositol, nicotinic acid, pyridoxine-HCl thiamine-HCl and combinations thereof.

The solid and liquid culture media preferably each comprise $CaCl_2$ in a concentration comprised from 120 to 170 mg/L, preferably from 130 to 160 mg/L; $KNO_3$ in a concentration comprised from 800 to 3700 mg/L, preferably from 1000 to 3100 mg/L; $MgSO_4$ in a concentration comprised from 220 to 270 mg/L, preferably from 230 to 260 mg/L, $NaH_2PO_4$ in a concentration comprised from 100 to 180 mg/L, preferably from 110 to 150 mg/L; and $(NH_4)_2SO_4$ in a concentration comprised from 100 to 180 mg/L, preferably from 110 to 150 mg/L.

The solid and liquid culture media preferably each comprise $CoCl_2 \cdot 6H_2O$ in a concentration comprised from 0.01 to 0.05 mg/L, preferably from 0.015 to 0.03 mg/L; $CuSO_4 \cdot 5H_2O$ in a concentration comprised from 0.01 to 0.05 mg/L, preferably from 0.015 to 0.03 mg/L; $NaEDTA \cdot 2H_2O$ in a concentration comprised from 20 to 60 mg/L, preferably from 30 to 45 mg/L; $FeSO_4 \cdot 7H_2O$ in a concentration comprised from 15 to 45 mg/L, preferably from 20 to 35 mg/L; $H_3BO_3$ in a concentration comprised from 1 to 7 mg/L, preferably from 2 to 5 mg/l; KI in a concentration comprised from 0.1 to 2 mg/L, preferably from 0.4 to 1 mg/L; $MnSO_4 \cdot H_2O$ in a concentration comprised from 5 to 20 mg/L, preferably from 7 to 15 mg/L; $Na_2MoO_4.2H_2O$ in a concentration comprised from 0.1 to 0.5 mg/L, preferably from 0.15 to 0.3 mg/L and $ZnSO_4 \cdot 7H_2O$ in a concentration comprised from 0.5 to 5 mg/L, preferably from 1 to 3 mg/L.

Both the solid and liquid culture media preferably each comprise myo-inositol in a concentration comprised from 70 to 130 mg, preferably from 90 and 110 mg; pyridoxine-HCl from 70 to 130 mg, preferably from 90 to 110 mg; and thiamine-HCl from 5 to 20 mg/L, preferably from 7 to 15 mg/L.

After step 1), the callus tissue is preferably divided into a plurality of portions that are stabilized through successive transfers into the solid culture medium (step 1a)), so as to obtain stabilized cells. This step takes the name of stabilization step.

After the stabilization step 1a), the stabilized cells preferably undergo a first "clonal selection". The clonal selection consists in culturing the stabilized cells for an adequate duration, preferably 5 to 20 days of culture, more preferably 10 to 15 days (step 1b). The cells are incubated in the dark at a temperature comprised from 15° C. to 35° C., preferably from 24° C. to 26° C.

In step 2), a plurality of cellular clones is isolated by taking aggregates of stabilized cells from the solid culture medium.

In step 3) the cellular clones are each inoculated into the liquid culture medium described above.

According to one embodiment, after a phase of growth for a time such as to obtain an appropriate multiplication of the cellular clone, preferably 10 to 15 days, in step 4) the polysaccharide content of each clone is determined.

In step 5) of selection of the cellular clone, a second clonal selection according to step 1b) is preferably carried out until obtaining a plant cell line of *Rosa* wherein the production of polysaccharides, preferably with a medium molecular weight, is optimal.

In a preferred embodiment, the clonal selection of the step 5) is repeated until obtaining a cell line of *Rosa* which comprises an amount of polysaccharides greater than 25% w/w, preferably comprised from 25% to 70% w/w, more preferably comprised from 30% to 65% w/w.

The polysaccharides present in the selected cell line comprise from 50% to 90%, preferably from 55% to 85%, of medium molecular weight polysaccharides.

The polysaccharides present in the selected cell line comprise from 20% to 30%, preferably from 25% to 35%, of low molecular weight polysaccharides.

In other words, the selected cell line comprises an amount of medium molecular weight polysaccharides comprised from 15% to 60% w/w, preferably comprised from 18% to 50% w/w, and an amount of low molecular weight polysaccharides comprised from 5% to 20% w/w, preferably comprised from 8% to 15% w/w, relative to the dry mass of the cell line.

In one embodiment, said selected cell line comprises an amount of polyphenols greater than 0.2% w/w, preferably comprised from 0.3% to 20% w/w, more preferably comprised from 0.4% to 18% w/w.

The cell line derived from the species *Rosa canina* preferably comprises an amount of polyphenols comprised from 3% to 25% w/w, preferably from 4% to 20% w/w.

The cell line derived from the species *Rosa chinensis* preferably comprises an amount of polyphenols comprised from 0.3% to 10% w/w, preferably from 0.4% to 8% w/w.

In one embodiment, the polyphenols are selected from flavonoids and non-flavonoids, wherein the flavonoids are preferably selected from catechin, epicatechin, procyanidin and proanthocyanidin. The polyphenols are preferably selected from catechin and proanthocyanidin, preferably types P2, P3 and P4 (P stands for the polymer and the numbers 2, 3 and 4 represent the number of catechin monomers contained in the molecule).

The non-flavonoids are selected from hydroxybenzoic acids, preferably gallic acid, and hydroxycinnamic acids, preferably selected from coumaric acid and caffeic acid. In a preferred embodiment, the cell line comprises an amount of proteins comprised from 10 to 40% w/w, preferably comprised from 12% to 38% w/w, more preferably comprised from 15% to 35% w/w.

In a preferred embodiment, the cell line comprises an amount of hydroxyproline comprised from 0.1 to 1.3% w/w, preferably comprised from 0.2% to 1.2% w/w, more preferably comprised from 0.3% to 1% w/w.

In a preferred embodiment, the cell line comprises an amount of lipids comprised from 1 to 10% w/w, preferably comprised from 2% to 8% w/w, more preferably comprised from 3% to 6% w/w.

The cell line derived from the species *Rosa canina* is preferably the line Rc-F2P comprising 30-55% w/w of polysaccharides, of which 65-80% are medium molecular weight polysaccharides and, preferably, 5-15% w/w of total polyphenols, 15-20% w/w of proteins and 0.2-0.6% w/w of hydroxyproline.

The cell line derived from the species *Rosa Chinensis* is preferably the line Rch-PsMW comprising 30-60% w/w of polysaccharides, of which 65-80% are medium molecular weight polysaccharides and, preferably, 0.5-5% w/w of total polyphenols, 16-35% w/w of proteins and 0.7-1.2% w/w of hydroxyproline.

A second aspect of the present invention relates to a derivative of the cell line which is a phytocomplex or an extract of the selected meristematic cell line as described above.

Phytocomplex means: dried or lyophilized cells, a cellular homogenate, or the cell walls and the components thereof. The phytocomplex is preferably a cellular homogenate.

Said phytocomplex comprises an amount of polysaccharides greater than 25% w/w, preferably comprised from 25% to 70% w/w, more preferably comprised from 30% to 65% w/w.

The polysaccharides present in the phytocomplex comprise from 50% to 90%, preferably from 55% to 85%, of medium molecular weight polysaccharides.

The polysaccharides present in the phytocomplex comprise from 20% to 30%, preferably from 25% to 35%, of low molecular weight polysaccharides.

In other words, the phytocomplex comprises an amount of medium molecular weight polysaccharides comprised from 15% to 60% w/w, preferably comprised from 18% to 50% w/w, and an amount of low molecular weight polysaccharides comprised from 5% to 20% w/w, preferably comprised from 8% to 15% w/w, relative to the dry mass of the phytocomplex.

The phytocomplex also further comprises an amount of proteins from 10 40% w/w, preferably from 12% to 38% w/w, more preferably comprised from 15% to 35% w/w, relative to the dry mass of phytocomplex.

The phytocomplex also further comprises an amount of hydroxyproline comprised from 0.1 to 1.3% w/w, preferably comprised from 0.2% to 1.2% w/w, more preferably comprised from 0.3% to 1% w/w relative to the dry mass of the phytocomplex.

The phytocomplex also further comprises an amount of lipids from 1 to 10% w/w, preferably from 2 to 8% w/w, preferably from 3 to 6% w/w relative to the dry mass of the phytocomplex.

In a preferred embodiment, said phytocomplex is derived from said selected meristematic cell line Rc-F2P or is derived from said selected meristematic cell line Rch-PsMW. The phytocomplex is preferably a cellular homogenate of the selected meristematic cell line Rc-F2P or is a cellular homogenate of the selected meristematic cell line Rch-PsMW.

Extract means an extract in an alcoholic solvent, for example in methanol or ethanol, or a water/ethanol mixture in different proportions: 50:50 or 60:40 or 70:30, of the cell line itself or a phytocomplex of the cell line. The extract is preferably an extract of a cellular homogenate of the line. The content of said extract corresponds to the content of the phytocomplex or cell line from which it was derived, with the variability due to the extraction technique.

A third aspect of the present invention relates to a composition comprising the meristematic cell line and/or a derivative thereof (phytocomplex and/or extract) in association with at least one excipient that is accepted from a cosmetic, nutraceutical and/or pharmaceutical viewpoint.

In one embodiment, the composition comprises the cell line and/or a derivative thereof in a concentration comprised from 0.01% to 30% w/w, preferably from 0.03% to 15% w/w, more preferably from 0.05% to 10% w/w relative to the weight of the composition.

In one embodiment, the cell line and/or a derivative thereof are dispersed before being mixed with the excipients to prepare the composition of the invention. By way of example, suitable dispersing agents are glycerine, propylene glycol or butylene glycol.

The composition of the present invention comprises at least one excipient acceptable for pharmaceutical, nutraceutical and/or cosmetic use, which is useful in the preparation of the composition and is generally biologically safe and nontoxic.

Said excipient can be at least one conditioning, humectant, or occlusive agent, a surfactant, a stabilizing agent, a preservative or an emollient for the skin.

The composition of the invention is formulated for topical use as a cream, gel-cream, gel, serum, oil, emulsion, emulsion-gel (emulgel) ointment, eye drops, mouthwash, spray, preferably nasal spray or stick (such as lip balm). The formulation of the composition as a face serum or as a cream, preferably a hand cream or face cream, for example with moisturizing, anti-wrinkle, antioxidant and/or cicatrizing activity, is particularly preferred.

The composition can also be formulated for oral administration, preferably as a pill, capsule, tablet, granular powder, hard-shelled capsule, orally dissolving granule, sachet or lozenge.

In one embodiment, the composition is formulated to release the active ingredients contained therein rapidly, or in a delayed and/or controlled manner after administration, preferably formulated as a liposome.

The experimental data included herein indicate that the cell line or a derivative thereof as described above is capable of exerting an antioxidant (reduction of free radicals), hydrating and cicatrizing effect.

In particular, the Applicant has demonstrated the ability of a derivative of the cell line to decrease the levels of free radicals and increase the expression of aquaporins, in particular aquaporin 3, which are involved in maintaining skin hydration and in the wound healing process.

Furthermore, the cell line obtained by the Applicant shows a high content of hydroxyproline, which represents about 20% of the amino acids of the glycoproteins present in the walls of plant cells. These glycoproteins rich in hydroxyproline include extensins, which are structurally similar to animal collagen. For this reason, numerous aspects of extensins are of cosmetic interest.

A further aspect of the present invention relates to the cosmetic use of the cell line or a derivative thereof.

Cosmetic use means the prevention, attenuation and/or combatting of the signs of the skin aging, hydration of the skin or cornea, anti-wrinkle activity and antioxidant activity.

A further aspect of the present invention relates to the cell line or a derivative thereof for use as a medication, in particular for the treatment or prevention of pathological conditions affecting the skin, preferably irritations, topical inflammation, cracking or reddening or to accelerate wound healing processes (cicatrizing effect).

A further aspect of the present invention relates to the use of the cell line or a derivative thereof as a dietary supplement to prevent or attenuate or combat the signs of skin aging and/or the increase in free radicals and/or systemic or skin dehydration. In this case, the cell line or a derivative thereof is formulated in compositions for oral use, such as a pill, capsule, tablet, granular powder, hard-shelled capsule, orally dissolving granule, sachet or lozenge.

Another aspect of the present invention relates to the use of the cell line or a derivative thereof for personal care and hygiene; in this case the line or a derivative thereof is formulated as a bath foam, shower gel, soap, shampoo or hair conditioner, together with suitable excipients.

Another aspect of the present invention relates to a process for preparing and selecting plant meristematic cells with a high polysaccharide content, preferably with a polysaccharide content greater than 25% w/w relative to the dry mass of the cell line. Said method comprises the steps of:
1) plating tissues obtained from a plant of the genus *Rosa* onto a solid culture medium;
2) isolating the cellular clones;
3) inoculating each of the isolated clones into a liquid culture medium;
4) determining the polysaccharide content for each clone;
5) selecting the cellular clone with the highest polysaccharide content.

In one embodiment, the preparation of meristematic cells entails collecting tissue, preferably of shoots from plants selected from the species *Rosa canina* and/or *Rosa chinensis*, washing it, for example with water, fragmenting it into small pieces and sterilizing it on plates, for example with successive treatments with ethanol, sodium hypochlorite and a mercury salt.

In a preferred embodiment of the invention, the solid and liquid culture media comprise salts suitable for the growth of plant cells, sucrose, naphthylacetic acid (NAA) and 6-benzyl-amino purine (BAP).

The solid culture media further comprises agar, whereas the liquid culture media does not contain agar.

The solid and liquid culture media preferably each comprise sucrose in a concentration comprised from 10 to 45 g/L, preferably from 15 to 40 g/L; NAA in a concentration comprised from 0.5 to 2.5 mg/L, preferably from 0.8 to 2 mg/L, and BAP in a concentration comprised from 0.1 to 0.5 mg/L, preferably from 0.15 to 0.3 g/L.

In both the solid and liquid culture media, the salts suitable for the growth of plant cells are selected from: $CaCl_2$, $KNO_3$, $MgSO_4$, $NaH_2PO_4$, $(NH_4)_2SO_4$ and combinations thereof.

In both the solid and liquid culture media, the salts suitable for the growth of plant cells are preferably selected from: $CoCl_2 \cdot 6H_2O$, $CuSO_4 \cdot 5H_2O$, $NaEDTA \cdot 2H_2O$, $FeSO_4 \cdot 7H_2O$, $H_3BO_3$, KI, $MnSO_4 \cdot H_2O$, $Na_2MoO_4 \cdot 2H_2O$, $ZnSO_4 \cdot 7H_2O$ and combinations thereof.

Both the solid and liquid culture media further comprise vitamins suitable for the growth of plant cells, preferably selected from: myo-inositol, nicotinic acid, pyridoxine-HCl, thiamine-HCl and combinations thereof.

In one embodiment, in both the solid and liquid culture media, the salts suitable for the growth of plant cells are selected from: $CaCl_2$, $KNO_3$, $MgSO_4$, $NaH_2PO_4$, $(NH_4)_2SO_4$, $CoCl_2 \cdot 6H_2O$, $CuSO_4 \cdot 5H_2O$, $NaEDTA \cdot 2H_2O$, $FeSO_4 \cdot 7H_2O$ $H_3BO_3$, KI, $MnSO_4 \cdot H_2O$, $Na_2MoO_4 \cdot 2H_2O$, $ZnSO_4 \cdot 7H_2O$ and combinations thereof. This combination of salts is the medium Gamborg B5.

In one embodiment, both the solid and liquid culture media, in addition to the salts specified above, further comprise vitamins suitable for the growth of plant cells selected from: myo-inositol, nicotinic acid, pyridoxine-HCl thiamine-HCl and combinations thereof.

The solid and liquid culture media preferably each comprise $CaCl_2$ in a concentration comprised from 120 to 170 mg/L, preferably from 130 to 160 mg/L; $KNO_3$ in a concentration comprised from 800 to 3700 mg/L, preferably from 1000 to 3100 mg/L; $MgSO_4$ in a concentration comprised from 220 to 270 mg/L, preferably from 230 to 260 mg/L, $NaH_2PO_4$ in a concentration comprised from 100 to 180 mg/L, preferably from 110 to 150 mg/L; and $(NH_4)_2SO_4$ in a concentration comprised from 100 to 180 mg/L, preferably from 110 to 150 mg/L.

The solid and liquid culture media preferably each comprise $CoCl_2 \cdot 6H_2O$ in a concentration comprised from 0.01 to 0.05 mg/L, preferably from 0.015 to 0.03 mg/L; $CuSO_4 \cdot 5H_2O$ in a concentration comprised from 0.01 to 0.05 mg/L, preferably from 0.015 to 0.03 mg/L; $NaEDTA.2H_2O$ in a concentration comprised from 20 to 60 mg/L, preferably from 30 to 45 mg/L; $FeSO_4 \cdot 7H_2O$ in a concentration comprised from 15 to 45 mg/L, preferably from 20 to 35 mg/L; $H_3BO_3$ in a concentration comprised from 1 to 7 mg/L, preferably from 2 to 5 mg/I; KI in a concentration comprised from 0.1 to 2 mg/L, preferably from 0.4 to 1 mg/L; $MnSO_4 \cdot H_2O$ in a concentration comprised from 5 to 20 mg/L, preferably from 7 to 15 mg/L; $Na_2MoO_4 \cdot 2H_2O$ in a concentration comprised from 0.1 to 0.5 mg/L, preferably from 0.15 to 0.3 mg/L and $ZnSO_4 \cdot 7H_2O$ in a concentration comprised from 0.5 to 5 mg/L, preferably from 1 to 3 mg/L.

Both the solid and liquid culture media preferably each comprise myo-inositol in a concentration comprised from 70 to 130 mg, preferably from 90 to 110 mg; pyridoxine-HCl from 70 to 130 mg, preferably from 90 to 110 mg; and thiamine-HCl from 5 to 20 mg/L, preferably from 7 to 15 mg/L.

After step 1), the callus tissue is preferably divided into a plurality of portions that are stabilised through successive transfers into the solid culture medium (step 1a)), so as to obtain stabilized cells. This step takes the name of stabilization step.

After the stabilization step 1a), the stabilized cells preferably undergo a first "clonal selection". The clonal selection consists in culturing the stabilized cells for an adequate duration, preferably 5 to 20 days of culture, more preferably 10 to 15 days (step 1b). The cells are incubated in the dark at a temperature comprised from 15° C. to 35° C., preferably from 24° C. to 26° C.

In step 2), a plurality of cellular clones is isolated by taking aggregates of stabilized cells from the solid culture medium.

In step 3) the cellular clones are each inoculated into the liquid culture medium described above.

According to one embodiment, after a phase of growth for a time such as to obtain an appropriate multiplication of the cellular clone, preferably from 10 and 15 days, in step 4) the polysaccharide content of each clone is determined.

In step 5) of selection of the cellular clone, a second clonal selection according to step 1b) is preferably carried out until obtaining a plant cell line of *Rosa* wherein the production of polysaccharides, preferably with a medium molecular weight, is optimal.

The selected cell line is then multiplied, in a flask or bioreactor or fermenter, so as to obtain an increase in the biomass.

The multiplication of the biomass takes place in a first step in a liquid growth medium. The liquid growth medium is a medium containing the Gamborg salts specified above, the vitamins listed above, sucrose NAA, and BAP.

The liquid growth medium, RP for *Rosa canina* and RPS for *Rosa chinensis*, contains, among Gamborg salts, $KNO_3$ in an amount comprised from 2 g/L to 4 g/L, preferably from 2 g/L to 3 g/L. Sucrose is preferably comprised from 20 g/L to 30 g/L. NAA is preferably comprised from 0.5 mg/L to 2 mg/L and BAP from 0.1 to 0.5.

The cells grown in the liquid growth medium are transferred, for the final phase of growth, into a final liquid medium, RP-F for *Rosa canina* and RPS-F for *Rosa chinensis*, containing the Gamborg salts listed above, the vitamins listed above and sucrose, which induces an increase in the polysaccharide content and the biomass.

The final liquid medium contains, among the Gamborg salts, $KNO_3$ in an amount comprised from 2 g/L to 5 g/L, preferably from 2 g/L to 4 g/L. Sucrose is preferably comprised from 25 g/L to 45 g/L. NAA is preferably comprised from 0.5 mg/L to 2 mg/L and BAP from 0.1 to 0.5 mg/L.

According to a preferred embodiment, the growth of the cell line in the flask, bioreactor or fermenter, both in the liquid growth medium and in the final liquid medium, is carried out at a temperature comprised from 15° C. to 35° C., typically about 25° C., for a period comprised from 7 to 30 days, preferably from 14 to 21 days, under conditions of darkness.

At the end of growth in the final liquid medium, the cell line is filtered and the cells are recovered in order to be used in the subsequent steps in the form of a phytocomplex, or else they may undergo a subsequent extraction phase in an alcohol solvent in order to produce a cell extract characterized by a high polysaccharide content.

The phytocomplex can be obtained by lyophilization or drying of live cells; in this case, the phytocomplex is a lyophilizate of dead cells.

In one embodiment, at the end of growth in the flask, bioreactor or fermenter the cells are homogenized, for example by mechanical disintegration, preferably in an acidified solution (for example with ascorbic acid or citric acid or acetic acid) and subsequently lyophilized or dried. In the latter case, the phytocomplex is a cellular homogenate wherein the cells and the internal structures thereof are disintegrated. These different types of phytocomplexes are all characterized in that they have a high polysaccharide content as previously described.

Alternatively, the phytocomplex, preferably in the form of a cellular homogenate, undergoes extraction in an alcohol solvent (for example methanol or ethanol) using conventional techniques. The extract thus obtained is characterized by a high polysaccharide content as detailed above and can be used for the preparation of cosmetic or pharmaceutical compositions as described above.

Alternatively, the live cells as such, following purification, can be directly employed for the preparation of the compositions of the invention.

EXAMPLES

Generation and Selection of the Meristematic Cell Lines of *Rosa canina* and *Rosa chinensis*

The induction of callus tissue was achieved using standard procedures described in the literature. The procedure provides for the collection of young tissues (shoots) from plants of *Rosa canina* and *Rosa Chinensis*, the cleaning thereof, for example with running water, minute fragmentation into 2-5 cm pieces and sanitization, for example by treatment, in sequence, with 70% ethanol in water for about 15', 2% sodium hypochlorite and 0.1% Tween 20 for about 5 minutes and, finally, at least 4 washes with sterile distilled water. Every fragment of plant tissue, broken down further (explants) is placed in Petri dishes containing a nutrient medium rendered solid by adding agar and supplemented with growth hormones. After a suitable period of incubation in the dark at 25° C., the undifferentiated callus tissue forms; it is then multiplied after transfer onto a larger surface with fresh medium.

The meristematic cells obtained are stabilized by means of a certain number of transfers (sub-cultures) onto solid culture media.

As regards the line of *Rosa canina*, the medium is a Gamborg B5 (Gamborg O. L. et al, 1968, Exp. Cell. Res., 50, 151) with 2.5 g/L of $KNO_3$ and the addition of 20 g/L of sucrose, 1 mg/L of NAA and 0.2 mg/L of BAP and 0.7-0.9% plant agar, final pH 6.5 (RP medium). The cell line obtained in this specific culture medium, after clonal selection performed in solid RP medium (with agar) and liquid RP medium (without agar), was called Rc-F2P. The belonging of the meristematic cells obtained to the botanical species *Rosa canina* was confirmed by DNA fingerprint analysis.

The medium for *Rosa chinensis* is a Gamborg B5 with 2.5 g/l of $KNO_3$ and the addition of 25 g/L of sucrose, 1.5 mg/L of NAA and 0.25 mg/L of BAP and 0.7-0.9% plant agar, pH finale 6.5 (RPS medium). The cell line obtained in this specific culture medium, after clonal selection performed in solid RPS medium (with agar) and liquid RPS medium (without agar) was called RCh-PsMW. The belonging of the meristematic cells obtained to the botanical species *Rosa chinensis* was confirmed by DNA fingerprint analysis.

The selected plant cell lines were multiplied to obtain sufficient amounts of biomass to be transferred into the liquid culture medium (RP and RPS medium without agar).

After growth in the RP and RPS liquid medium, the cell suspensions were transferred into bioreactors containing the final productive medium (RP-F or RPS-F) or the liquid growth medium (RP or RPS without agar) for further phases of growth.

The productive liquid medium for *Rosa canina* is a Gamborg B5 with the addition of 30 g/L of sucrose, a total of 3 g/L $KNO_3$, 1 mg/L of NAA and 0.2 mg/L of BAP, final pH 6.5 (RP-F medium).

The productive liquid medium for *Rosa chinensis* is a Gamborg B5 with the addition of 35 g/L of sucrose, a total of 3 g/L of $KNO_3$, 1.5 mg/L of NAA and 0.25 mg/L of BAP, final pH 6.5 (RPS-F medium).

At the end of growth in the productive medium, the cell suspensions are filtered and the biomasses are recovered and used for the subsequent steps of preparing the phytocomplexes.

The characteristics of the cell lines of *Rosa canina* and *Rosa chinensis* will be described by way of non-limiting example.

Morphological Characteristics of the Cell Line

Figure 2:
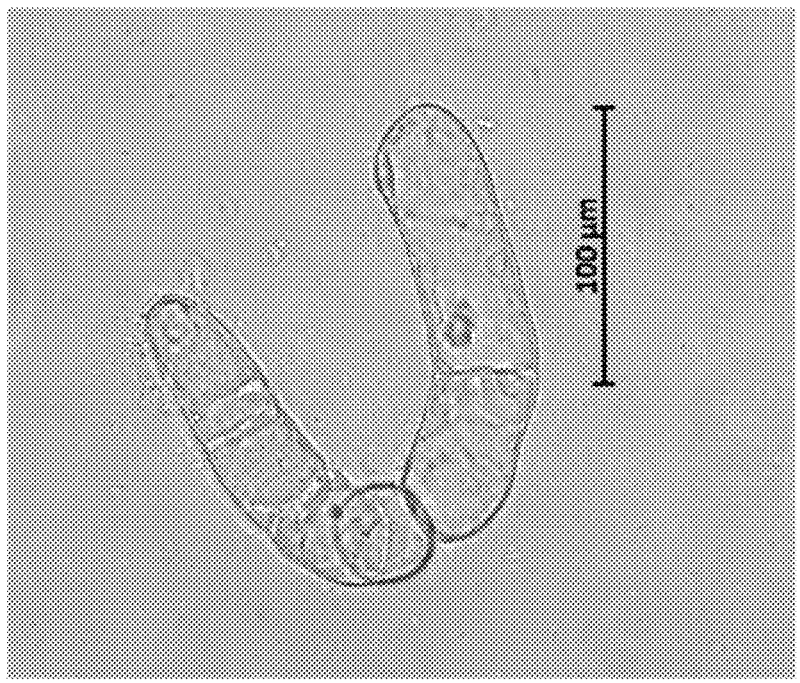
FIG. 2 shows a magnification (200×) of a portion of FIG. 1.
Figure 3:
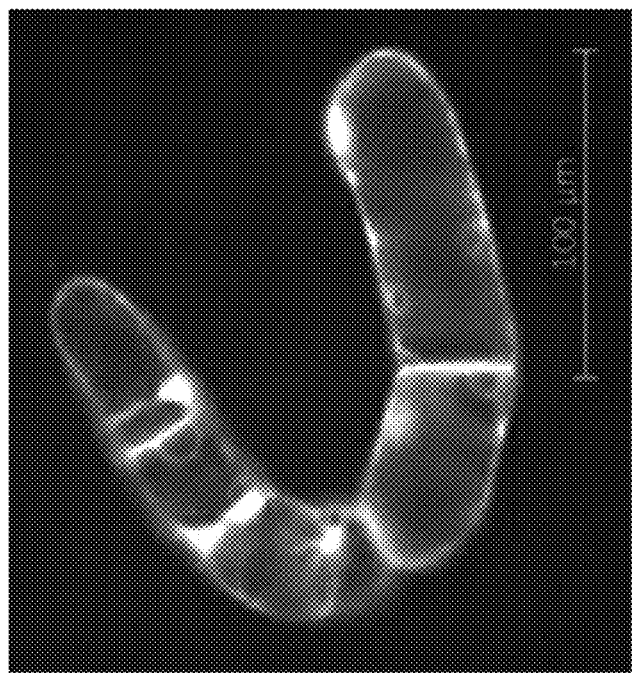
FIG. 3 shows a magnification (200×) of a portion of FIG. 1 after staining with fluorescein diacetate.

The selected cell line of *Rosa canina*, called Rc-F2P, is maintained in the solid RP culture medium, is hazelnut-coloured with beige reflections and has a friable texture (FIGS. 1-3).

Figure 4:
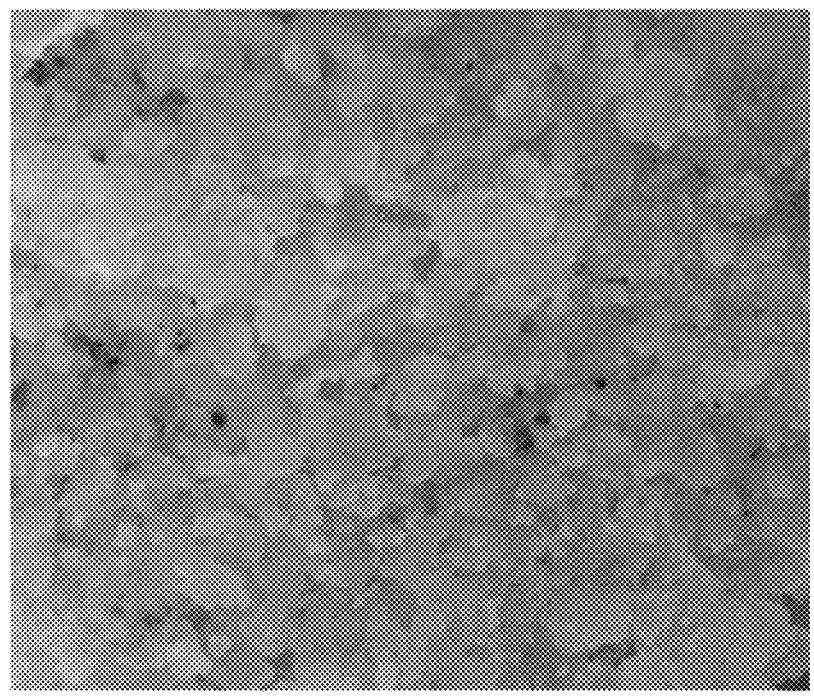
FIG. 4 shows a photo, taken with a bright-field optical microscope, of the cell line called Rch-PsMW, maintained in a solid medium.
Figure 5:
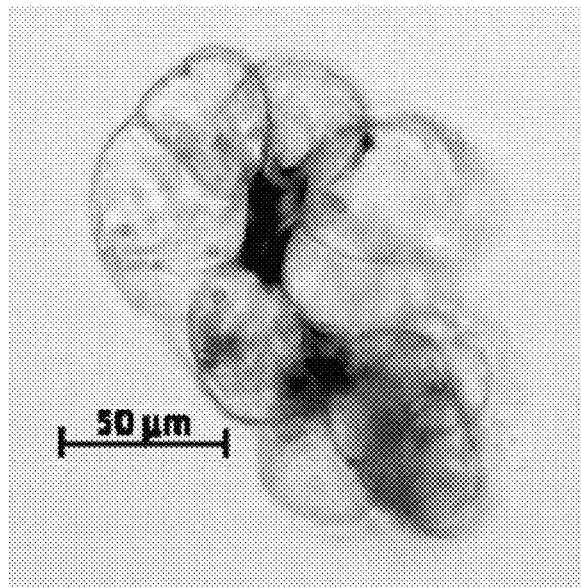
FIG. 5 shows a bright-field magnification (200×) of a portion of FIG. 4.
Figure 6:
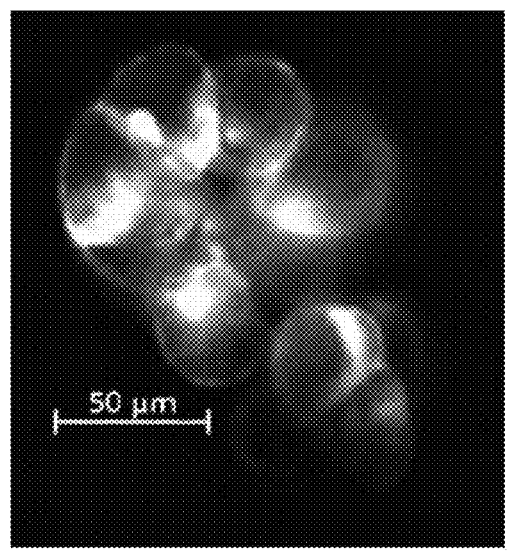
FIG. 6 shows a magnification (200×) of a portion of FIG. 4 after staining with fluorescein diacetate.

The selected cell line of *Rosa chinensis*, called Rch-PsMW, is maintained in the solid RPS culture medium, is pale yellow in colour with brown spots and has a friable texture (FIG. 4-6).

Homogenization Procedure

The procedure for homogenizing the biomasses of cells selected and grown in bioreactors comprises the following steps:

a) filtration of the biomass obtained from the growth of the Rc-F2P or Rch-PsMW cell cultures in the productive liquid culture medium RP-F in the case of the line Rc-F2P or RPS-F in the case of the line Rch-PsMW, in order to have only cells and discard the medium;

b) washing of the cells with a double volume, relative to the cells, of saline solution (0.9% W/V NaCl in sterile water);

c) addition of 1.5% w/w (from 0.5 to 2% w/w) of ascorbic acid (or citric acid or a mixture of citric and ascorbic acid) to the filtered, washed biomass;

d) homogenization of the mixture, for example with an Ultra-Turrax or any other instrument suitable for breaking down the cells and the internal structures thereof;

e) drying of the biomass by lyophilization or air circulation drying or rotating cylinder drying or fluid bed drying or atomization.

Using the procedure described for the lines Rc-F2P and Rch-PsMW, one obtains the homogenate A) or B), respectively:

A) homogenate of the cell line Rc-F2P with a high content of medium molecular weight polysaccharides in RP-F medium, after 14 days of growth in the dark at 25° C. (±2).

Description of the Content of Homogenate A), Rc-F2P:
30-55% polysaccharides, of which 65-80% are medium molecular weight polysaccharides;
5-15% total polyphenols;
15-20% proteins;
0.2-0.6% hydroxyproline;
3-5% lipids;
2-4% moisture;
2-4% ash;
5-30% citric acid.

B) homogenate of the cell line Rch-PsMW with a high content of medium molecular weight polysaccharides in RPS-F medium, after 14 days of growth in the dark at 25° C. (±2).

Description of Homogenate B), Rch-PsMW:
30-60% polysaccharides, of which 65-80% are medium molecular weight polysaccharides;
0.5-5% total polyphenols;
16-35% proteins;
0.7-1.2% of hydroxyproline;
3-6% lipids;
2-5% moisture;
2-6% ash;
5-30% citric acid.

Examples of preparation of the cell lines Rc-F2P in RP-F medium and Rch-PsMW in RPS-F medium are provided by way of non-limiting example.

Preparation and Analysis of the Rc-F2P Phytocomplex

Meristematic cells, stabilized and selected as previously described, deriving from the line of *Rosa canina* called Rc-F2P, cultured in solid RP medium (Gamborg B5 with the addition of 20 g/L of sucrose, 1 mg/L of NAA and 0.2 mg/L of BAP, final pH 6.5 and containing 0.8% (W/V) agar) were inoculated into 5 flasks with a 1-litre capacity, containing 200 ml of RP-F liquid medium (Gamborg B5 with the addition of 30 g/L of sucrose, a total of 3 g/L of $KNO_3$, 1 mg/L of NAA and 0.2 mg/L of BAP, final pH 6.5). The amount of meristematic cells inoculated into the liquid medium was equal to 6% W/V. The suspensions thus obtained were incubated in the dark at 25° C. and placed on top of an orbital shaker set on 120 RPM. After 14 days of incubation the plant biomass (1 litre of cell suspension) was collected and filtered over a nylon mesh with a porosity of 50 μm and washed with 900 ml of sterile saline solution (0.9% W/V). The washed cells (fresh weight 450 g) were supplemented with 8 g of citric acid and homogenized with an Ultra-Turrax.

The homogenized cells were lyophilized. 42.71 g of lyophilizate (homogenate of meristematic cells of *Rosa canina* called Rc-F2P) with a content of total polyphenols equal to 5.21 g, total polysaccharides of 19.2 g (of which 15.3 g are medium molecular weight polysaccharides), 6.7 g of proteins, 2 g of lipids, 0.9 g of ash and 7.5 g of citric acid was obtained from 1 litre of cell suspension (Table 1).

TABLE 1

Characterization of the homogenate of the line Rc-F2P

|  | g/42.71 g of product | % w/w |
|---|---|---|
| Polyphenols | 5.21 | 12 |
| Total polysaccharides | 19.2 (of which 15.3 with a medium molecular weight) | 45 (35.9 with a medium molecular weight) |
| Proteins | 6.7 (of which 0.19 g of hydroxyproline) | 15.68 (0.44% of hydroxyproline) |
| Lipids | 2.0 | 4.6 |
| Ash | 0.9 | 2.1 |
| Citric acid | 7.5 | 17.5 |
| Moisture | 1.2 | 2.8 |

The characterization of the homogenate was carried out using the methods described below:

a) Quantification of Total Polyphenols in the Cell Line Rc-F2P with Folin-Ciocalteau Folin-Ciocalteau reagent is a bright yellow aqueous solution of phosphotungstic and phosphomolybdic acid. The method exploits the redox reaction, in a basic environment, between compounds with a reducing character and Folin-Ciocalteau reagent, from which blue chromogenic complexes are formed, whose intensity grows with increases in the amount of reducing compounds present, which can be detected at 725 nm. Analysis by means of Folin-Ciocalteau reagent makes it possible to carry out a quantitative spectrophotometric determination of the phenolic compounds and reducing substances present in the sample, which are expressed as gallic acid.

20 mg of phytocomplex Rc-F2P were weighed and extracted in 10 ml methanol/water 50:50 in an ultrasonic bath for 20 minutes. As a reference, standard solutions of gallic acid were used at concentrations of 200-20 μg/mL for the construction of calibration curve. Then, 0.5 mL of solution containing the extract was drawn and 0.5 mL of a solution of sodium carbonate 20% w/v and 0.5 mL of Folin Ciocalteau were added. The mixture was then brought to a volume of 10 mL with deionized water and the solution obtained was left to rest in the dark away from sources of heat for 30 minutes. The five standard solutions of gallic acid were treated in the same manner as the extracts.

The solutions were read at 725 nm by means of a UV-Vis spectrophotometer. The of total polyphenols is expressed as a % of gallic acid and is shown in table 2.

TABLE 2

| Extract | % polyphenols (expressed as equivalents in gallic acid) |
|---|---|
| Line RcF2P | 12 ± 0.10 | b) UPLC-qTOF Analysis of the Cell Line RcF2P

The cellular homogenate powder was extracted with 6 volumes of methanol for 15 minutes in a sonicator at 40 Hz under ice, after having been stirred with a shaker for 30 seconds; the extract was recovered after centrifugation at 18000 g for 10 minutes at 4° C. The extract was diluted 1:5 with methanol and subsequently diluted 1:2 with double-distilled water. The extract was filtered and analysed by UPLC-qTOF. The platform used consisted in an Acquity UPLC I-class (Waters) provided with a refrigerated autosampler and coupled online with a UV/VIS detector of the diode array type and with a high-resolution mass spectrometer of the Xevo G2-XS QTof 4k type (Waters).

Use was made of a C18 "reverse phase" chromatography column, Acquity UPLC BEH C18 100×2.1 mm, 1.7 μm particles (Waters), preceded by a guard column.

The elution conditions were the following:

Solvent A: 0.1% of formic acid in water;

Solvent B: 100% acetonitrile.

TABLE 3 elution method.

| Time from start of the analysis (in min) | duration of the gradient (in min) | solvent B, % |
|---|---|---|
| Start |  | 1 |
| 0 | 1 | 1 |
| 1 | 9 | 40 |
| 10 | 1 | 99 |
| 11 | 1 | 99 |

Figure 7:
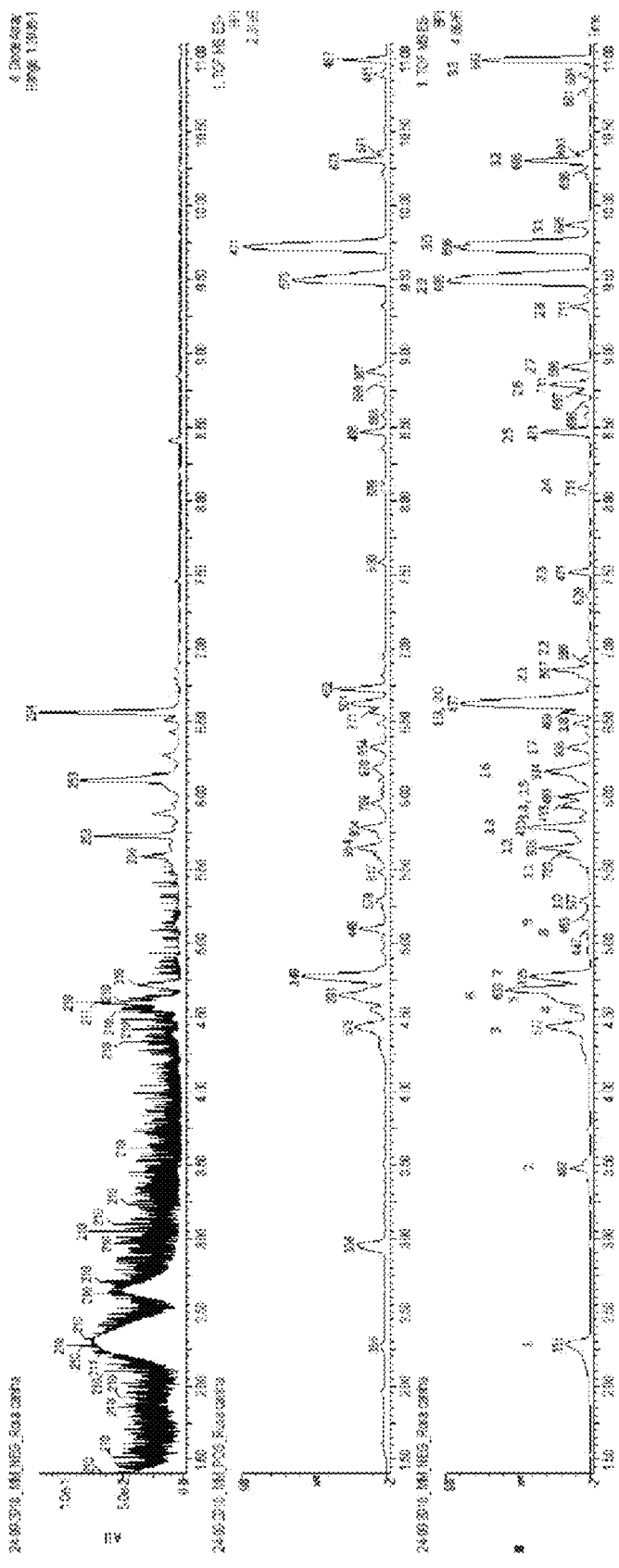
FIG. 7 shows a UV/VIS chromatogram obtained by means of a diode array detector and UPLC-MS chromatograms (qTOF) obtained in the positive and negative ionization modes.

FIG. 7 shows the UV/VIS chromatogram obtained via the diode array detector and the UPLC-MS chromatograms (qTOF) obtained in the positive and negative ionization modes. Table 4 indicates the id, the value of m/z and, where possible, the identification of the main peaks.

FIG. 8 indicates the id, the value of m/z and, where possible, the identification of the main peaks.

The identification was conducted through the value of m/z in the negative mode, a comparison with the literature and the fragmentation pattern. Furthermore, a targeted analysis of the putative favan-3-ols and proanthocyanidins was performed. From this further analysis that was performed, it emerged that the phytocomplex of meristematic cells of *Rosa canina* contains significant amounts of catechin and proanthocyanidins types P2, P3 and P4 (P stands for the polymer and the numbers 2, 3 and 4 represent the number of catechin monomers contained in the molecule).

c) Quali-Quantitative Analysis of the Polysaccharide Content of the Cell Line Rc-F2P The analysis was conducted by HPLC-ELSD-SEC (size exclusion chromatography). 50 mg of powder of the homogenate of the cell line Rc-F2P were weighed and dissolved in 25 ml of water. The samples were sonicated for 30 minutes, centrifuged and placed in vials.

HPLC-SEC analysis enables compounds to be separated based on their molecular size, which is a representation of their molecular weight: compounds with a low to medium molecular weight (glucose-dextran 1000) will have longer retention times, since they remain in the column for a longer time than polysaccharides with a higher molecular weight. As a reference standard, use was made of glucose as a monosaccharide (MW 180 Da) and dextran with different molecular weights, in particular 1000 and 5000 Da.

A 300×7.8 mm PolySep-GFC-P 3000 column with a 5×7.8 mm guard column was used as the stationary phase, whilst 0.1M ammonium acetate and acetonitrile (99:1) were used as the mobile phase. A Sedex 60 LT evaporative light scattering detector (ELSD) was used as the detector. The gain was set at 9 au, the pressure at 2.3 bar and the evaporation temperature at 60 degrees.

Figure 9:
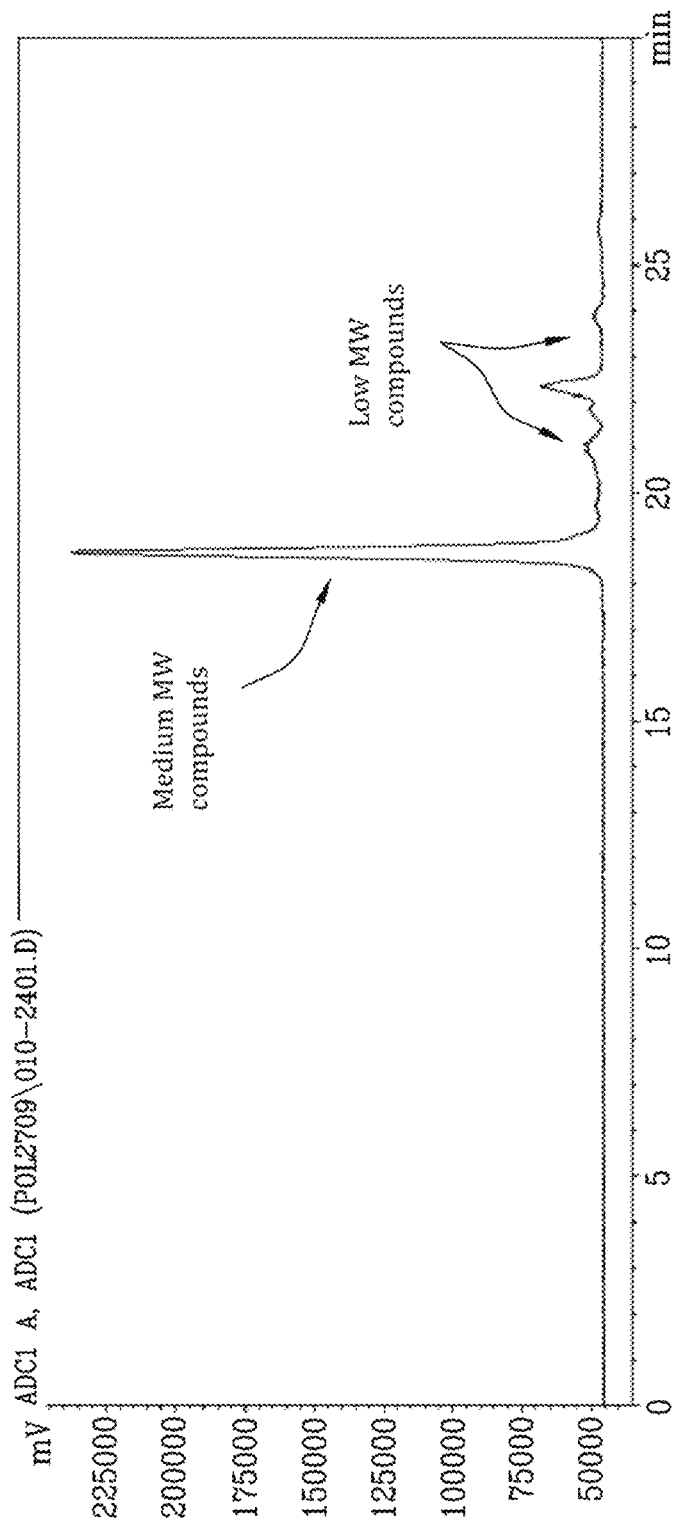
FIG. 9 shows a chromatogram of the extract of the Rc-F2P phytocomplex analysed by HPLC-ELSD-SEC (size exclusion chromatography).

Based on the analyses performed, it emerged that the polysaccharides of the homogenate of *Rosa canina* are distinguished by a pattern of substances that exhibit low molecular weight peaks comparable to that of glucose (21-22 minutes, such compounds can be mono- and disaccharides) and peaks falling in the region attributable to 1000 Da (19 minutes). FIG. 9 shows the chromatogram of the homogenate of the phytocomplex of *Rosa canina* analysed.

The results obtained are shown in table 4.

TABLE 4

| Sample | % low molecular weight polysaccharides expressed like glucose | % medium-high molecular weight polysaccharides expressed as dextran 1000 Da | Total |
|---|---|---|---|
| Rc-F2P phytocomplex | 9.12 ± 0.78 | 35.94 ± 0.82 | 45.06 | d) Analysis of the Protein Content of Cell Line Rc-F2P

A determination of the total content of protein nitrogen was conducted on the cell line Rc-F2P using the Kjeldahl method, as described in Lynch, J M. et al, "Kjeldahl nitrogen analysis as a reference method for protein determination in dairy products" Journal of AOAC International (1999), 82(6), 1389-1398.

The protein content in the line Rc-F2P proved to be equal to 15.68% W/W.

e) Analysis of the Hydroxyproline Content of the Cell Line Rc-F2P

The hydroxyproline content of the cell line Rc-F2P was determined by HPLC analysis after hydrolysis with HCl 6N and derivation of the amino acids with o-phthaldialdehyde (OPA). The analytic determinations were repeated in triplicate. The content of hydroxyproline was equal to 447 mg in 100 g of dry cell line (0.44% W/W of Hyp in the cell line).

f) Analysis of the Lipid Content of the Cell Line Rc-F2P

The extraction of the total lipid fraction was carried out on the line Rc-F2P by Soxhlet extraction with dichloromethane, extended for at least 12 hours according to the method described in Martinez M. et al, "Soxhlet lipids extraction from cotton from different producing areas. Comparison of dichloromethane or successive dichloromethane-methanol extractions". Grasas y Aceites (1997), 48 (4), 226-230. The lipid content in the cell line Rc-F2P was equal to 4.6% W/W.

g) Analysis of Moisture and Ash in the Line Rc-F2P

A determination of moisture was carried out on the homogenate of the cell line by leaving the material in a stove at 40° C. for 12 hours. The determination of ash was obtained by treating the material in a muffle furnace at 300° C. until arriving at a constant weight.

The moisture of the phytocomplex was equal to 2.8%, whilst the ash was equal to 2.1%.

Preparation and Analysis of the Rch-PsMW Phytocomplex

Meristematic cells, stabilized and selected as previously described, deriving from the line of *Rosa chinensis*, called Rch-PsMW, cultured in solid RPS Medium (Gamborg B5 with the addition of 25 g/L of sucrose, 1.5 mg/L of NAA and 0.25 mg/L of BAP and 0.8% plant agar, final pH 6.5) were inoculated into 5 flasks with a 1-litre capacity, containing 200 ml of RPS-F liquid medium (Gamborg B5 with the addition of 35 g/L of sucrose, 3 g/L of KNO3, 1.5 mg/L of NAA and 0.25 mg/L of BAP, final pH 6.5). The amount of meristematic cells inoculated into the liquid medium was equal to 5% W/V. The suspensions thus obtained were incubated in the dark at 25° C. and placed on top of an orbital shaker set on 120 RPM. After 14 days of incubation the plant biomass (1 litre of cell suspension) was collected and filtered over a nylon mesh with a porosity of 50 μm and washed with 900 ml of sterile saline solution (0.9% W/V). The washed cells (fresh weight 480 g) were supplemented with 6 g of ascorbic acid and homogenized with an Ultra-Turrax.

The homogenized cells were lyophilized. 45.25 g of lyophilizate (homogenate of meristematic cells of *Rosa chinensis* called Rch-PsMW) with a content of total polyphenols equal to 2.15 g, total polysaccharides of 15.38 g (of which 9.9 g are medium molecular weight polysaccharides), 16 g of proteins, 2.8 g of lipids, 0.9 g of ash and 5.5 g of citric acid was obtained from 1 litre of cell suspension (Table 5).

TABLE 5

Characterization of the homogenate of the line Rch-PsMW.

| | g/45.25 g of product | % w/w |
|---|---|---|
| Polyphenols | 2.15 | 4.7 |
| Total polysaccharides | 15.38 (of which 9.9 g with a medium molecular weight) | 34 (22 with a medium molecular weight) |
| Proteins | 16.0 (of which 0.45 are hydroxyproline) | 35 (0.9% is hydroxyproline) |
| Lipids | 2.8 | 6 |
| Ash | 0.99 | 2.18 |
| Citric acid | 5.5 | 12.1 |
| Moisture | 2.43 | 5.3 |

The characterization of the phytocomplex was carried out using the methods described below:

a) Quantification of Total Polyphenols in the Cell Line Rch-PsMW with Folin-Ciocalteau The method used was described previously. The results obtained are shown in table 6.

TABLE 6

| Extract | % polyphenols (expressed as equivalents in gallic acid) |
|---|---|
| Line Rch-PsMW) | 2.15 ± 0.10 | b) UPLC-qTOF Analysis of the Cell Line Rch-PsMW

The analysis was performed as described for the line Rc-F2P.

Figure 10:
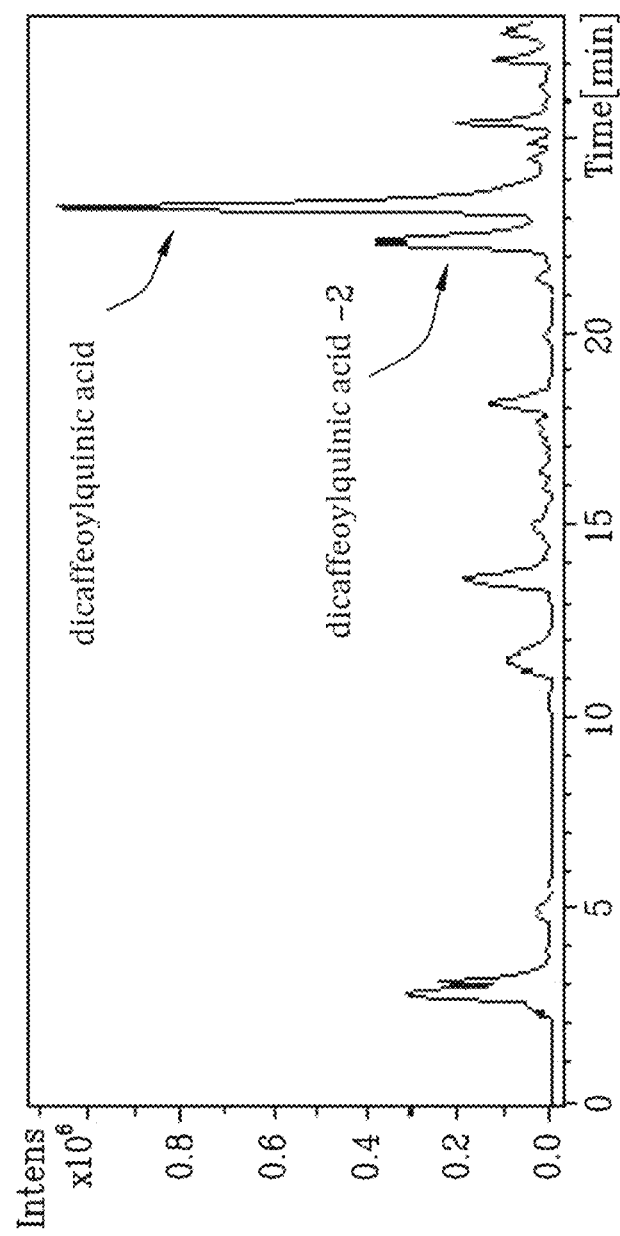
FIG. 10 shows a chromatogram of the extract of the Rc-F2P phytocomplex analysed by HPLC-ELSD-SEC of the Rch-PsMW phytocomplex.

FIG. 10 shows the UV/VIS chromatogram obtained via the diode array detector and the UPLC-MS chromatograms (qTOF) obtained in the negative ionization mode.

c) Quali-Quantitative Analysis of the Polysaccharide Content in the Cell Line Rch-PsMW The analysis was conducted as described for the line Rc-F2P.

Figure 11:
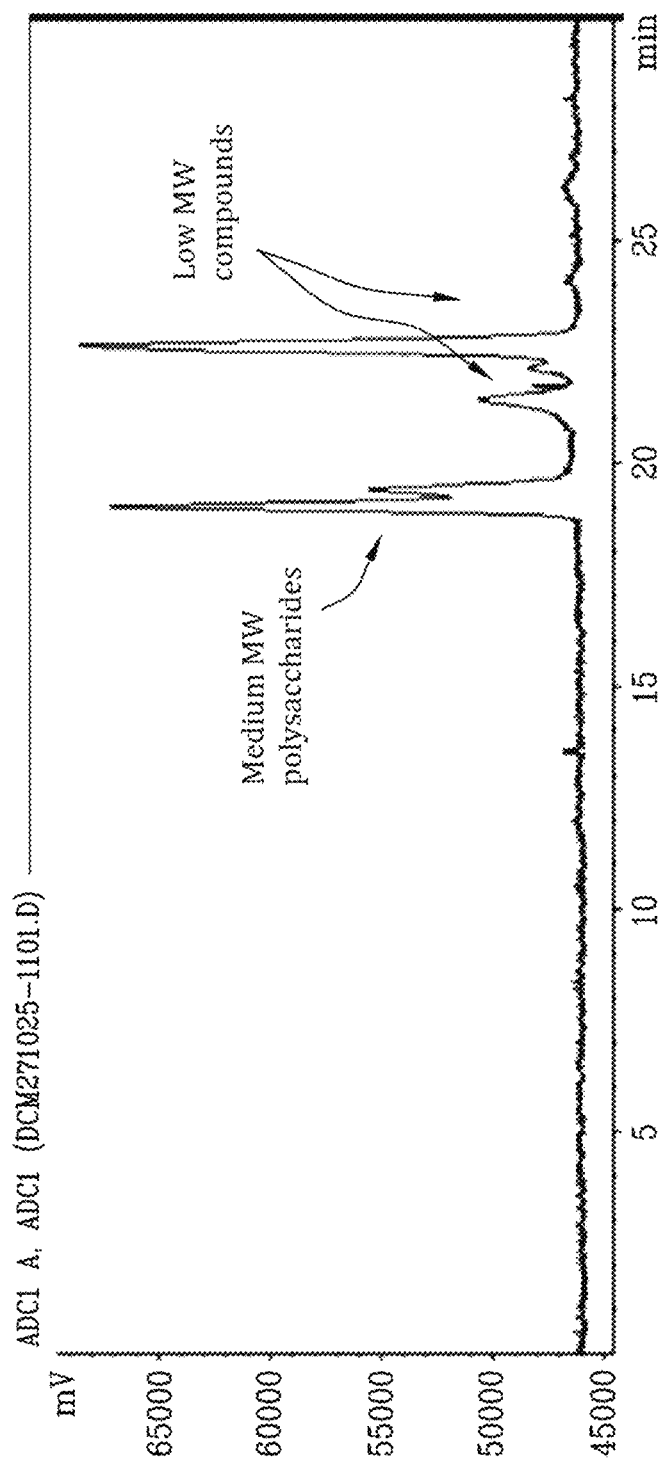
FIG. 11 shows a chromatogram of the extract of the Rch-PsMW phytocomplex analysed by HPLC-ELSD-SEC.

FIG. 11 shows the chromatogram of the line Rch-PsMW analysed.

The results obtained are shown in table 7.

d) Analysis of the Hydroxyproline Content of the Cell Line Rch-PsMW

The hydroxyproline content of the cell line Rch-PsMW was determined by HPLC analysis after hydrolysis with HCl 6N and derivation of the amino acids with o-phthaldialdehyde (OPA). The analytic determinations were repeated in triplicate. The content of hydroxyproline was equal to 996 mg in 100 g of dry cell line (0.99% W/W of Hyp in the phytocomplex cell line).

TABLE 7

| Sample | % low molecular weight polysaccharides expressed like glucose | % medium-high molecular weight polysaccharides expressed | Total |
| --- | --- | --- | --- |
| Rch-PsMW homogenate | 12 ± 0.78 | 22 ± 0.82 | 34.00 |

Preparation of the Cell Line Rc-F2P on an Industrial Scale

Meristematic cells, stabilized and selected as previously described, deriving from the line of *Rosa canina* called Rc-F2P, cultured in solid RP medium (Gamborg B5 with the addition of 20 g/L of sucrose, 1 mg/L of NAA, 0.2 mg/L of BAP and 0.8% W/V of plant agar, final pH 6.5) were inoculated into 10 flasks with a 1-litre capacity, containing 200 ml of RP liquid medium. The amount of meristematic cells inoculated into the liquid medium was equal to 6% W/V. The suspensions thus obtained were incubated in the dark at 25° C. and placed on top of an orbital shaker set on 120 RPM. After 7 days of incubation the cell suspensions were used to inoculate 10 flasks with a 3-litre capacity, containing 800 ml of RP liquid medium. 200 ml of the cell suspension was transferred into 800 ml of RP medium contained in a flask with a 3-litre capacity. The suspensions thus obtained were incubated in the dark at 25° C. and placed on top of an orbital shaker set on 120 RPM. After 7 days of incubation the cell suspensions were used to inoculate a bioreactor containing 90 litres of RP-F medium (Gamborg B5 with the addition of 30 g/L of sucrose, a total of 3 g/L of $KNO_3$, 1 mg/L of NAA and 0.2 mg/L of BAP, final pH 6.5).

After 14 days of growth in the bioreactor the plant biomass (100 litres of cell suspension) was collected and filtered over a nylon mesh with a porosity of 50 μm and washed with 64 L of sterile saline solution (0.9% W/V). The washed cells (fresh weight 32 kg) were supplemented with 320 g of citric acid and homogenized with an Ultra-Turrax.

The homogenized cells were dried. 4090 g of homogenate Rc-F2P were obtained from 100 litres of cell suspension.

Preparation of the Cell Line Rch-PsMW on an Industrial Scale

Meristematic cells, stabilized and selected as previously described, deriving from the line of *Rosa chinensis* called Rch-PsMW, cultured in solid RPS Medium (Gamborg B5 with the addition of 25 g/L of sucrose, 1.5 mg/L of NAA, 0.25 mg/L of BAP and 0.8% of plant agar W/V, final pH 6.5) were inoculated into 10 flasks with a 1-litre capacity, containing 200 ml of RPS liquid medium. The amount of meristematic cells inoculated into the liquid medium was equal to 6% W/V. The suspensions thus obtained were incubated in the dark at 25° C. and placed on top of an orbital shaker set on 120 RPM. After 7 days of incubation the cell suspensions were used to inoculate 10 flasks with a 3-litre capacity, containing 800 ml of RPS liquid medium. 200 ml of the cell suspension was transferred into 800 ml of RPS medium contained in a flask with a 3-litre capacity The suspensions thus obtained were incubated in the dark at 25° C. and placed on top of an orbital shaker set on 120 RPM. After 7 days of incubation the cell suspensions were used to inoculate a bioreactor containing 90 litres of RPS-F medium (Gamborg B5 with the addition of 35 g/L of sucrose, 3 g/L of $KNO_3$, 1.5 mg/L of NAA and 0.25 mg/L of BAP, final pH 6.5).

After 14 days of growth in the bioreactor the plant biomass (100 litres of cell suspension) was collected and filtered over a nylon mesh with a porosity of 50 μm and washed with 70 L of sterile saline solution (0.9% W/V). The washed cells (fresh weight 35 kg) were supplemented with 350 g of citric acid and homogenized with an Ultra-Turrax.

The homogenized cells were dried. 4450 g of Rch-PsMW homogenate were obtained from 100 litres of cell suspension.

Biological Test of Antioxidant Activity with the Cell Line Rc-F2P

The assay of antioxidant activity was performed using the DPPH method. The assay with the DPPH (2,2-diphenyl-1-picryl-hydrazyl) radical has the aim of evaluating, in vitro, the antioxidant activity of the line of *Rosa canina* Rc-F2P vis-à-vis a stained stable radical and measuring its disappearance by spectrophotometry.

The methanol solution of DPPH is purple in colour and shows maximum absorbance at a wavelength 517 nm. When DPPH is reacted with an antioxidant compound capable of yielding a hydrogen radical, a destaining of the solution from purple to yellow occurs, due to the disappearance of the DPPH radical, which can be monitored over time spectrophotometrically at the wavelength of maximum absorbance, 517 nm.

The Rc-F2P homogenate of meristematic cells of *Rosa canina* was extracted in methanol and placed in an ultrasonic bath for 20 minutes. Various aliquots of solution were taken and they were added to a same amount of DPPH solution and brought to volume with methanol, so as to evaluate the antioxidant capacity of the sample at different concentrations. The results are expressed as EC50, i.e. as the concentration of the Rc-F2P phytocomplex capable of decreasing the initial absorbance of the radical at 517 nm by 50%. The result is then compared with that obtained from a methanol solution of ascorbic acid, used as a reference. The lower the EC50, the greater the antioxidant capacity.

Table 8 shows the antioxidant activity of the homogenate of the line Rc-F2P.

TABLE 8

| Sample | EC50 µg/mL |
|---|---|
| Homogenate Rc-F2P | 38.82 ± 5.71 |
| Ascorbic acid (reference) | 3.19 ± 0.16 |

Biological Test on the Increase in the Biosynthesis of Aquaporins-3 on Reconstructed Skin with the Cell Line Rch-PsMW The evaluation of the increase in the expression of aquaporins-3 was carried out at the VitroScreen laboratories (Milan) using homeostatic reconstructed human epidermis (RHE) models. The evaluation of the increase in the biosynthesis of aquaporins-3 by the Rch-PsMW line of Rosa chinensis was carried out using both topical applications (15 µl of a saline solution containing 0.1% w/w of cellular homogenate) and systemic applications (0.1% w/w of homogenate in the maintenance culture medium of the microtissue) on RHE.

After the topical application, the RHE was incubated for 24 hours (at 37° C. 5% CO2). The systemic application was carried out by adding 0.1% of extract into the maintenance culture medium of the epidermis and incubating the RHE for 24 hours.

Figure 12:
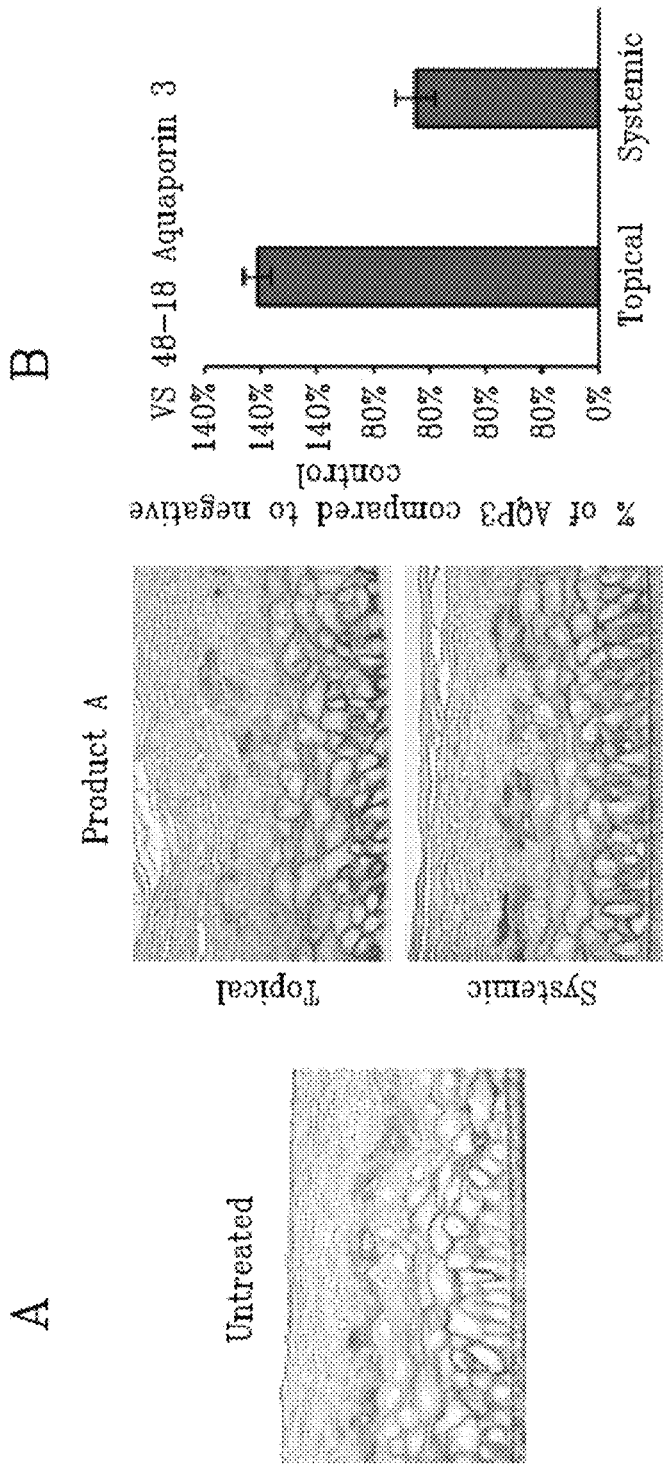
FIG. 12 shows, in (A) the immunostaining of aquaporins-3 using fast red stain (24 hours after treatment). In (B), the signal intensity was quantified and expressed as a % increase in the colour compared to the negative control.

After incubation, the microtissues were collected in order to perform an immunostaining analysis and PCR. To evaluate the expression of aquaporins-3, use was made of an immunohistochemical technique that envisaged the use of the anti-aquaporin-3 antibody (Abcam), followed by an evaluation of antigen-antibody binding using a fluorescence microscope. FIG. 12 illustrates the results obtained as regards the increase in the biosynthesis of aquaporins-3.

Aquaporin-3 is involved in maintaining skin hydration and in wound healing. The Rch-PsMW homogenate favours the biosynthesis of aquaporin-3 transmembrane, thereby favouring the transport of water.

Formulation of the Lines Rch-PsMW and Rc-F2P in Two-Phase and Multiple Emulsions, in Gels and in Skin and Hair Cleansing Systems The homogenate of the line Rch-PsMW or of the line Rc-F2P was dispersed in glycerine at a concentration of 3% w/w (INCI NAME: Glycerin (and) Rosa chinensis Callus Lysate (and) Citric Acid). The dispersion was added at 3% to the formulas described below.

TABLE 9

Emulsions (two-phase and multiple O/A, A/O, A/S, A/O/A)

| Ingredients | % |
|---|---|
| Water | 60-95 |
| Aqueous phase rheology modifiers (polysaccharides, proteins, synthetic polymers, inorganic polymers) | 0.1-3 |
| Emollient lipids (natural oils and butters, synthetic lipids, silicones) | 1-30 |
| Natural and synthetic waxes | 0-10 |
| Emulsifier (ionic, non-ionic, silicone, polymeric) | 0.1-5 |
| Fatty alcohols | 0-5 |
| Preservative system | 0-2 |
| Glycerin (and) Rosa Chinensis Callus Lysate (and) Citric Acid | 3 |

TABLE 10

Gel formulations

| Ingredients | % |
|---|---|
| Water | 70-98 |
| Humectants | 0-20 |
| Rheology modifiers (polysaccharides, proteins, synthetic polymers, inorganic polymers) | 0.1-20 |
| Emollient lipids (natural oils and butters, synthetic lipids, silicones) | 0-10 |
| Emulsifiers (ionic, non-ionic, silicone, polymeric) | 0-2 |
| Conditioning agents (protein hydrolysates, amino acids, quaternary polymers) | 0-5 |
| Preservative system | 0-2 |
| Glycerin (and) Rosa Chinensis Callus Lysate (and) Citric Acid | 3 |

TABLE 11

Skin and hair cleansing systems

| Ingredients | % |
|---|---|
| Water | 70-98 |
| Surfactants (ionic, non-ionic, polymeric) | 1-30 |
| Emollient lipids (natural oils and butters, synthetic lipids, silicones) | 0-5 |
| Emulsifiers (ionic, non-ionic, silicone, polymeric) | 0-2 |
| Conditioning agents (protein hydrolysates, amino acids, quaternary polymers) | 0-10 |
| Humectants | 0-10 |
| Preservative system | 0-2 |
| Glycerin (and) Rosa Canina Callus Lysate (and) Citric Acid | 3 |

The invention claimed is:

1. A meristematic cell line derived from a plant belonging to the genus Rosa, wherein said cell line is obtained by means of a process comprising the steps of:
   1) plating a tissue obtained from a plant of the genus Rosa onto a solid culture medium;
   2) isolating a plurality of cellular clones;
   3) inoculating each of the isolated clones into a liquid culture medium;
   4) determining the polysaccharide content for each clone;
   5) selecting the cellular clone with the highest polysaccharide content,
      wherein the solid and liquid culture media comprise salts suitable for the growth of plant cells, sucrose, naphthylacetic acid (NAA) and 6-benzyl amino purine (BAP) and
      wherein the meristematic cell line comprises an amount of polysaccharides greater than 25% w/w.

2. The meristematic cell line according to claim 1, wherein the solid and liquid culture media each comprise sucrose in a concentration comprising 10 to 45 g/L.

3. The meristematic cell line according to claim 1, wherein in both the solid and liquid culture media, the salts suitable for the growth of plant cells are selected from: $CaCl_2$, $KNO_3$, $MgSO_4$, $NaH_2PO_4$, $(NH_4)_2SO_4$ and combinations thereof.

4. The meristematic cell line according to claim 1, wherein in both the solid and liquid culture media, the salts suitable for the growth of plant cells are selected from: $CoCl_2 \cdot 6H_2O$, $CuSO_4 \cdot 5H_2O$, $NaEDTA \cdot 2H_2O$, $FeSO_4 \cdot 7H_2O$, $H_3BO_3$, KI, $MnSO_4 \cdot H_2O$, $Na_2MoO_4 \cdot 2H_2O$, $ZnSO_4 \cdot 7H_2O$ and combinations thereof.

5. The meristematic cell line according to claim 1, wherein both the solid and liquid culture media further comprise vitamins suitable for the growth of plant cells selected from:
  myo-inositol, nicotinic acid, pyridoxine-HCl, thiamine-HCl and combinations thereof.

6. The meristematic cell line according to claim 3, wherein both the solid and liquid culture media each comprise $CaCl_2$ in a concentration from 120 to 170 mg/L; $KNO_3$ in a concentration comprising 800 to 3700 mg/L; $MgSO_4$ in a concentration comprising 220 to 270 mg/L, $NaH_2PO_4$ in a concentration comprising 100 to 180 mg/L; and $(NH_4)_2SO_4$ in a concentration comprising 100 to 180 mg/L.

7. The meristematic cell line according to claim 4, wherein the solid and liquid culture media each comprise $CoCl_2·6H_2O$ in a concentration comprising 0.01 to 0.05 mg/L; $CuSO_4·5H_2O$ in a concentration comprising 0.01 to 0.05 mg/L; $NaEDTA·2H_2O$ in a concentration comprising 20 to 60 mg/L; $FeSO_4·7H_2O$ in a concentration comprising 15 to 45 mg/L; $H_3BO_3$ in a concentration comprising 1 to 7 mg/L; KI in a concentration comprising 0.1 to 2 mg/L; $MnSO_4·H_2O$ in a concentration comprising 5 to 20 mg/L; $Na_2MoO_4·2H_2O$ in a concentration comprising 0.1 to 0.5 mg/L and $ZnSO_4·7H_2O$ in a concentration comprising 0.5 to 5 mg/L.

8. The meristematic cell line according to claim 5, wherein both the solid and liquid culture media each comprise myo-inositol in a concentration comprising 70 to 130 mg;
  pyridoxine-HCl from 70 to 130 mg; and thiamine-HCl from 5 to 20 mg/LL.

9. The meristematic cell line according to claim 1, comprising an amount of medium molecular weight polysaccharides comprising 50% to 90%, relative to the total amount of polysaccharides.

10. The meristematic cell line according to claim 1 comprising an amount of low molecular weight polysaccharides comprising 20% to 30%, relative to the total amount of polysaccharides.

11. The meristematic cell line according to claim 1, comprising an amount of polyphenols greater than 0.2%, relative to the dry mass of the cell line.

12. The meristematic cell line according to claim 11, derived from the species *Rosa canina*, comprising an amount of polyphenols comprising 3% to 25%, relative to the dry mass of the cell line.

13. The meristematic cell line according to claim 11, derived from the species *Rosa chinensis*, comprising an amount of polyphenols comprising 0.3% to 10%, relative to the dry mass of the cell line.

14. The meristematic cell line according to claim 1, comprising proteins in an amount of from 10% to 40% w/w, lipids in an amount from 1% to 10% w/w relative to the dry mass of the cell line, and hydroxyproline in an amount comprising 0.1 to 1.3% w/w, relative to the dry mass of the cell line.

15. A composition comprising the meristematic cell line according to claim 1.

16. The composition according to claim 15, comprising the meristematic cell line in a concentration comprising 0.01% to 1% by weight, relative to the total composition.

17. The composition according to claim 15, formulated as a cream, gel cream, gel, serum, oil, emulsion, emulsion gel (emulgel), ointment, eye drops, mouthwash, spray, preferably nasal spray, stick, pill, capsule, tablet, granular powder, hard-shelled capsule, orally dissolving granule, sachet, lozenge or liposome.

18. A meristematic cell line according to claim 1, wherein the plant belongs to the species *Rosa canina* or to the species *Rosa chinensis*.

19. A meristematic cell line according to claim 1, wherein the amount of polysaccharides comprises 25% to 70% w/w, relative to the dry mass of the cell line.

20. A process for preparing and selecting plant meristematic cells derived from a plant belonging to the genus *Rosa*, said cells having a polysaccharide content greater than 25% w/w relative to the dry mass of the cell line, said process comprising the steps of:
  1) plating a tissue obtained from a plant of the genus *Rosa*, onto a solid culture medium;
  2) isolating a plurality of cellular clones;
  3) inoculating each of the isolated clones into a liquid culture medium;
  4) determining the polysaccharide content for each clone;
  5) selecting the cellular clone with the highest polysaccharide content,
    wherein the solid and liquid culture media comprise salts suitable for the growth of plant cells, sucrose, naphthylacetic acid (NAA) and 6-benzyl-amino purine (BAP).

* * * * *